US007485373B2

(12) United States Patent
Krzysik et al.

(10) Patent No.: US 7,485,373 B2
(45) Date of Patent: Feb. 3, 2009

(54) LOTIONED TISSUE PRODUCT WITH IMPROVED STABILITY

(75) Inventors: Duane G. Krzysik, Appleton, WI (US); Stephen Baldwin, Menasha, WI (US); Bozena Nogaj, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 332 days.

(21) Appl. No.: 10/659,968

(22) Filed: Sep. 11, 2003

(65) Prior Publication Data

US 2005/0058833 A1    Mar. 17, 2005

(51) Int. Cl.
*B32B 23/04* (2006.01)
(52) U.S. Cl. ............... 428/532; 428/535; 428/536; 428/537.5; 428/153; 428/154; 424/400; 424/401; 424/402
(58) Field of Classification Search .......... 428/532, 428/535, 536, 537.5, 153, 154; 424/400, 424/401, 402
See application file for complete search history.

(56) References Cited

U.S. PATENT DOCUMENTS

| | | | |
|---|---|---|---|
| 3,301,746 A | 1/1967 | Sanford et al. | |
| 3,812,000 A | 5/1974 | Salvucci et al. | |
| 3,814,096 A | 6/1974 | Weiss et al. | |
| 3,896,807 A | 7/1975 | Buchalter | |
| 3,974,025 A | 8/1976 | Ayers | |
| 4,112,167 A | 9/1978 | Dake et al. | |
| 4,191,609 A | 3/1980 | Trokhan | |
| 4,208,459 A | 6/1980 | Becker et al. | |
| 4,300,981 A | 11/1981 | Carstens | |
| 4,637,859 A | 1/1987 | Trokhan | |
| 4,690,821 A | 9/1987 | Smith et al. | |
| 4,798,603 A | 1/1989 | Meyer et al. | |
| 4,962,133 A | 10/1990 | Chromecek et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,221,534 A | 6/1993 | DesLauriers et al. | |
| 5,509,915 A | 4/1996 | Hanson et al. | |
| 5,520,917 A | 5/1996 | Mizuguchi et al. | |
| 5,525,345 A | 6/1996 | Warner et al. | |
| 5,612,045 A | 3/1997 | Syverson | |
| 5,624,676 A | 4/1997 | Mackey et al. | |
| 5,705,164 A | 1/1998 | Mackey et al. | |
| 5,716,692 A | 2/1998 | Warner et al. | |
| 5,720,966 A | 2/1998 | Ostendorf | |
| 5,843,056 A | 12/1998 | Good et al. | |
| 5,855,999 A | 1/1999 | McCormack et al. | |
| 5,879,341 A | 3/1999 | Odorzynski et al. | |
| 6,063,335 A | 5/2000 | Pirolo et al. | |
| 6,146,648 A * | 11/2000 | Bret et al. ................ | 424/401 |
| 6,149,934 A | 11/2000 | Krzysik et al. | |
| 6,179,961 B1 * | 1/2001 | Ficke et al. ............... | 162/127 |
| 6,211,139 B1 * | 4/2001 | Keys et al. ................ | 510/504 |
| 6,217,890 B1 | 4/2001 | Paul et al. | |
| 6,238,682 B1 * | 5/2001 | Klofta et al. ............... | 424/402 |
| 6,261,580 B1 * | 7/2001 | Lehrter et al. ............. | 424/402 |
| 6,287,581 B1 | 9/2001 | Krzysik et al. | |
| 6,340,467 B1 | 1/2002 | Morrison | |
| 6,410,039 B1 | 6/2002 | Walker | |
| 6,428,794 B1 * | 8/2002 | Klofta et al. ............... | 424/401 |
| 6,433,068 B1 | 8/2002 | Morrison et al. | |
| 6,458,343 B1 * | 10/2002 | Zeman et al. .............. | 424/63 |
| 6,503,412 B1 * | 1/2003 | Schroeder ................. | 252/8.86 |
| 6,503,526 B1 | 1/2003 | Krzysik et al. | |
| 6,534,074 B2 | 3/2003 | Krzysik et al. | |
| 6,570,054 B1 * | 5/2003 | Gatto et al. ................ | 604/364 |
| 6,586,652 B1 * | 7/2003 | Roe et al. .................. | 604/364 |
| 6,627,787 B1 * | 9/2003 | Roe et al. .................. | 604/364 |
| 6,716,204 B1 | 4/2004 | D'Acchioli et al. | |
| 6,733,772 B1 * | 5/2004 | Bret et al. ................. | 424/443 |
| 6,825,393 B2 * | 11/2004 | Roe et al. .................. | 604/364 |
| 2001/0014350 A1 | 8/2001 | Krzysik et al. | |
| 2002/0128615 A1 | 9/2002 | Tyrrell et al. | |
| 2002/0128621 A1 | 9/2002 | Kruchoski et al. | |
| 2002/0136755 A1 | 9/2002 | Tyrrell et al. | |
| 2002/0165508 A1 | 11/2002 | Klofta et al. | |
| 2005/0058669 A1 | 3/2005 | Krzysik et al. | |

FOREIGN PATENT DOCUMENTS

EP          0497144 A1     8/1992

(Continued)

OTHER PUBLICATIONS

International Search Report from PCT/US2004/017636 dated Nov. 17, 2004.
International Search Report from PCT/US2004/019447 dated Feb. 21, 2005.
GELS, Internet article, http://www.penreco.com/products/gels/gels.asp, last checked Aug. 10, 2004.
International Search Report from PCT/US2004/011595 dated Sep. 1, 2004.
Flick, E.W., "Cosmetic and toiletry formulations", 1984, pp. 37, 154, Noyes Publications, United States, XP002303389.

(Continued)

*Primary Examiner*—Leszek Kiliman
(74) *Attorney, Agent, or Firm*—Armstrong Teasdale LLP

(57) ABSTRACT

Tissue products, such as bath tissue and facial tissue, comprising an improved lubricating formulation are disclosed. The lubricating formulation is applied to at least one surface of the tissue product and is stable at elevated temperatures, remains on or near the surface of the tissue product prior to use, and readily transfer the user=s skin upon use. The lubricating formulations described herein have a melt point viscosity of from about 5000 cPs to about 1,000,000 cps, and a process temperature viscosity of from about 50 cPs to about 50,000 cPs. The lubricating formulations comprise an emollient, a structurant, a rheology enhancer, and other optional components.

64 Claims, No Drawings

FOREIGN PATENT DOCUMENTS

| | | |
|---|---|---|
| WO | WO92/16216 A1 | 10/1992 |
| WO | WO99/45973 A1 | 9/1999 |
| WO | WO 00/64407 A1 | 11/2000 |
| WO | WO 00/64502 A1 | 11/2000 |
| WO | WO 00/64503 A1 | 11/2000 |
| WO | WO 00/69484 A1 | 11/2000 |
| WO | WO 02/05789 A2 | 1/2002 |
| WO | WO 02/34305 A2 | 5/2002 |
| WO | WO 03/004070 A1 | 1/2003 |
| WO | WO 03/005981 A2 | 1/2003 |
| WO | WO 03/028776 A1 | 4/2003 |
| WO | WO 03/037292 A1 | 5/2003 |
| WO | WO 03/039492 A1 | 5/2003 |
| WO | WO 2004/087092 A1 | 10/2004 |

* cited by examiner

LOTIONED TISSUE PRODUCT WITH IMPROVED STABILITY

BACKGROUND OF THE INVENTION

The present invention relates to tissue products comprising a lubricating formulation for transfer to the skin upon use. More particularly, the present invention relates to facial and bath tissue comprising a lubricating formulation comprising an emollient, a structurant, and a rheology enhancer. The novel lubricating formulation has improved stability and enhanced aesthetics, and transfers easily from the tissue to skin upon use.

Many absorbent tissue products, such as facial tissue, bath tissue, paper towels, and napkins are used to absorb and remove bodily fluids, make-up, and other soils, and leave the skin clean and dry. During repeated use, however, many tissue products can also abrade the skin and remove the natural protective oils and lipids from the skin=s surface. For example, during frequent nose blowing or anal cleansing, the skin may be compromised and can become so abraded as to become red and sore to the touch. In this state, additional irritants can penetrate the outer layers of the skin and cause further irritation, and even infection.

In order to address these concerns, there have been numerous previous attempts to reduce the abrasive effect of bath and facial tissues and to increase their softness impression. One common approach to increase the softness of tissue products is by closely controlling the mechanical processing of the tissue. By using particular processing steps during papermaking, bath and facial tissue products can be made that are softer and less irritating when used on the skin. Examples of tissue products that are mechanically processed to be softer are shown in U.S. Pat. No. 4,300,981 (Carstens), issued Nov. 17, 1981, as well as the various patents discussed in its specification.

Besides mechanical processing, others have applied emollients, salves, cleansing agents, and the like to tissue products to enhance not only the cleaning of the skin, but also to reduce irritation and inflammation by depositing a protective layer on the skin surface. This reduction in irritation and inflammation is typically achieved through either the lubricity of the substance applied to the tissue or through the therapeutic action of the substance itself. This approach is illustrated in U.S. Pat. No. 4,112,167 (Dake et al.) issued Sep. 5, 1978, particularly in regard to bath tissues. See also in U.S. Pat. No. 3,896,807 (Buchalter), issued Jul. 29, 1975 and in U.S. Pat. No. 3,814,096 (Weiss et al.), issued Jun. 4, 1974 for other examples of this approach.

One specific substance that has been applied as a lotion to tissue products to impart a soothing, lubricious feel is mineral oil. Mineral oil (also known as liquid petrolatum) is a mixture of various liquid hydrocarbons obtained by distilling the high-boiling (i.e., 300° C.-390° C.) fractions in petroleum. Mineral oil is liquid at ambient temperatures (i.e., 20° C.-25° C.). As a result, mineral oil is relatively fluid and mobile, even when applied to tissue products. Because mineral oil is fluid and mobile at ambient temperatures, it tends not to remain localized on the surface of the tissue, but instead migrates throughout the tissue matrix. Accordingly, relatively high levels of mineral oil need to be applied to the tissue to provide the desired softness and lotion-like feel. These levels can be as high as about 22 wt. % to about 25 wt. % of the tissue product. This leads not only to increased costs for these lotioned tissue products, but other detrimental effects as well.

One of these detrimental effects is a decrease in tensile strength of the tissue product. As mineral oil migrates to the interior of the tissue, it tends to act as a debonding agent, thus decreasing the tensile strength of the product. This debonding effect becomes more pronounced as the level of mineral oil applied is increased. Increasing the level of mineral oil applied can also adversely affect the caliper of the tissue product.

Even without increasing its level, the tendency of mineral oil to migrate into the interior of the tissue matrix once applied has other detrimental effects. For example, the applied mineral oil can transfer to, into, and through the packaging or wrapper material for the lotioned toilet tissue product. This can create the need for barrier-type packaging or wrapper films to avoid smearing or other leakage of mineral oil from the tissue product, which can result in significantly increased costs, as well as a messy package for consumers.

To date, most of the formulations, including formulations with mineral oil, have been liquids that require the addition of a high amount to the tissue to the point of feeling wet or oily in order for the formulation to transfer to the skin. Other formulations tried to date are semi-solid at room temperature, and require heating to be applied to the surface of the tissue where it is available to transfer to the user's skin. While much of the formulation does freeze on the surface of the tissue, some of the formulation penetrates to the inner portion of the tissue where it is unavailable for transfer to the skin, and may lead to one or more of the detrimental effects described above.

When applying a liquid or semi-solid lubricating formulation to a tissue product, there is always a balancing act required between applying the maximum amount of the formulation to the surface for transfer to the skin, while maintaining stability, and hence reducing the migration of the lubricating formulation or formulation components into the inner plies of the tissue product at elevated temperatures, such as those encountered during manufacturing, storage or transportation. Lubricating formulations that are too soft tend to migrate into the tissue product matrix as they do not hold the liquid portion of the semi-solid formulation. Lubricating formulations that are too hard do not transfer readily to the skin, and may flake off prior to use. As such, there is a need in the industry for lubricating formulations suitable for use in combination with tissue products that remain on the surface of the tissue, have less or no migration into the tissue product, and easily transfer to the skin surface during use without flaking to improve skin health.

SUMMARY OF THE INVENTION

The present invention provides tissue products, such as bath tissue and facial tissue, comprising an improved lubricating formulation. The lubricating formulation is stable at elevated temperatures, remains on or near the surface of the tissue product prior to use, and readily transfers to the user's skin upon use. The lubricating formulations described herein have a melt point viscosity as defined herein of from about 5000 cPs to about 1,000,000 cps, and a process temperature viscosity as defined herein of from about 50 cPs to about 50,000 cPs.

Specifically, the lubricating formulations comprise the following components:
(a) an emollient;
(b) a structurant;
(c) a rheology enhancer; and
(d) other optional components.

Other optional components suitable for use in the lubricating formulations described herein include, for example, moisturizers, humectants, vitamins, botanical extracts, skin protectants, astringents, lipids, sterols, powders, fragrances, antioxidants, colorants, preservatives, fragrances, optical brighteners, sunscreens, alpha hydroxy acids, and combinations thereof. Additionally, a hydrophilic surfactant may be utilized to emulsify various ingredients into the formulation, and improve wettability of the product.

Briefly, therefore, the present invention is directed to a tissue product for absorbing a liquid. The tissue product comprises a fibrous substrate material and a lubricating formulation. The lubricating formulation is present on the tissue in an amount of from about 1% (by weight of the dry tissue) to about 30% (by weight of the dry tissue) and comprises from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the formulation) of a rheology enhancer.

The present invention is further directed to a tissue product for absorbing a liquid. The tissue product comprises a fibrous substrate material and a lubricating formulation. The lubricating formulation is present on the tissue in an amount of from about 1% (by weight of the dry tissue) to about 30% (by weight of the dry tissue) and comprising from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the formulation) of a rheology enhancer. The lubricating formulation has a melt point viscosity of from about 5000 cPs to about 1,000,000 cPs and a process temperature viscosity of from about 50 cPs to about 50,000 cPs.

The present invention is further directed to a method of manufacturing a facial tissue. The method comprises introducing a lubricating formulation onto a tissue substrate wherein the lubricating formulation is present on the tissue substrate in an amount of from about 1% (by weight of the dry tissue) to about 30% (by weight of the dry tissue) and comprises from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the formulation) of a rheology enhancer. The lubricating formulation has a melt point viscosity of from about 5000 cPs to about 1,000,000 cPs and a process temperature viscosity of from about 50 cPs to about 50,000 cPs.

Other features and advantages of this invention will be in part apparent and in part pointed out hereinafter.

DETAILED DESCRIPTION OF THE PREFERRED EMBODIMENTS

In accordance with the present invention, it has been discovered that various types of rheology enhancers can be introduced into lubricating formulations for use in combination with a tissue product, such as facial tissue or bath tissue, to provide a lubricating formulation that remains on the surface of the tissue product and does not substantially migrate into the tissue matrix prior to use. Surprisingly, the rheology enhancers, which impart a specific melt point viscosity and process temperature viscosity to the lubricating formulation to significantly improve performance, do not substantially negatively affect the transfer of the lubricating formulation to the skin during use.

The tissue products of the present invention comprise a tissue substrate in combination with a lubricating formulation. As used herein, tissue products are meant to include facial tissue, bath tissue, towels, hanks, napkins and the like. The present invention is useful with tissue products and tissue paper in general, including but not limited to conventionally felt-pressed tissue paper; high bulk pattern densified tissue paper; and high bulk, uncompacted tissue paper. The tissue paper can be of a homogenous or multi-layered construction, and tissue paper products made therefrom can be of a single-ply or multi-ply construction. The tissue paper desirably has a basis weight of between about 10 $g/m^2$ and about 65 $g/m^2$, and density of about 0.6 g/cc or less. More desirably, the basis weight will be about 40 $g/m^2$ or less and the density will be about 0.3 g/cc or less. Most desirably, the density will be between about 0.04 g/cc and about 0.2 g/cc. Unless otherwise specified, all amounts and weights relative to the paper are on a dry basis. Tensile strengths in the machine direction can be in the range of from about 100 to about 5,000 grams per inch of width. Tensile strengths in the cross-machine direction are in the range of from about 50 grams to about 2,500 grams per inch of width. Absorbency is typically from about 5 grams of water per gram of fiber to about 9 grams of water per gram of fiber.

Conventionally pressed tissue paper and methods for making such paper are well known in the art. Such paper is typically made by depositing a papermaking furnish on a foraminous forming wire, often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided from a pressurized headbox, which has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The formed sheets are considered to be compacted since the entire web is subjected to substantial mechanical compressional forces while the fibers are moist and are then dried while in a compressed state.

High bulk pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non-ornamental configuration or can be formed so as to provide an ornamental design(s) in the tissue paper. Preferred processes for making pattern densified tissue webs are disclosed in U.S. Pat. No. 3,301,746 (Sanford et al.), issued Jan. 31, 1967; U.S. Pat. No. 3,974,025 (Ayers), issued Aug. 10, 1976; and U.S. Pat. No. 4,191,609

(Trokhan) issued Mar. 4, 1980; and U.S. Pat. No. 4,637,859 (Trokhan) issued Jan. 20, 1987; all of which are incorporated by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further de-densified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

Desirably, the furnish is first formed into a wet web on a foraminous forming carrier, such as a Fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally pre-dried to a selected fiber consistency from about 40% to about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000 (Salvucci et al.), issued May 21, 1974 and U.S. Pat. No. 4,208,459 (Becker et al.), issued Jun. 17, 1980, both of which are incorporated by reference. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least about 80%, and creping the web. Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25-50%, transferring the web to a thermal dryer such as a Yankee and creping the web. Overall, water is removed from the web by vacuum, mechanical pressing and thermal means. The resulting structure is strong and generally of singular density, but very low in bulk, absorbency and softness.

The papermaking fibers utilized in preparing tissue paper for the products of the present invention will normally include fibers derived from wood pulp. Other cellulosic fibrous pulp fibers, such as cotton linters, bagasse, etc., can be utilized and are intended to be within the scope of this invention. Synthetic fibers, such as rayon, polyethylene and polypropylene fibers, can also be utilized in combination with natural cellulosic fibers. One exemplary polyethylene fiber that can be utilized is Pulpex.RTM., available from Hercules, Inc. (Wilmington, Del.).

Applicable wood pulps include chemical pulps, such as Kraft, sulfite, and sulfate pulps, as well as mechanical pulps including, for example, groundwood, thermo-mechanical pulp and chemically modified thermo-mechanical pulp. Chemical pulps, however, are typically desirable since they impart a superior tactile sense of softness to tissue sheets made therefrom. Pulps derived from both deciduous trees and coniferous trees can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as bath tissue, paper towels, facial tissues and other similar products, high wet strength is a desirable attribute. Thus, it is often desirable to add to the papermaking furnish chemical substances known in the art as "wet strength" additives.

In addition to wet strength additives, it can also be desirable to include in the papermaking fibers certain dry strength and lint control additives known in the art. In this regard, starch binders have been found to be particularly suitable. In addition to reducing tinting of the finished tissue paper product, low levels of starch binders also impart a modest improvement in the dry tensile strength without imparting stiffness that could result from the addition of high levels of starch. Typically, the starch binder is included in an amount such that it is retained at a level of from about 0.01 to about 2%, preferably from about 0.1 to about 1%, by weight of the dry tissue paper. The lubricating formulations described herein for use in combination with the tissue product are either solid or semi-solid at room temperature. As used herein, the term semi-solid means that the lubricating formulation has a rheology typical of pseudoplastic or plastic fluids. When applied to the tissue product, the lubricating formulations described herein impart a soft, lubricious, lotion-like feel to the touch.

The lubricating formulation is transferred to the skin of the user upon use to improve the skin health of the user.

As noted above, the lubricating formulations of the present invention comprise an emollient, a structurant, and a rheology enhancer. Other optional components, such as surfactants, may also be included in the lubricating formulations as discussed herein.

An emollient is an active ingredient in a formulation that typically softens, soothes, supples, coats, lubricates and/or moisturizes the skin. Generally, emollients accomplish several of these objectives simultaneously. Typically, emollients suitable for use in the lubricating formulations described herein are fluids at room temperature such that they impart a soft, lubricious lotion-like feel upon use. The emollient is present in the lubricating formulation in an amount of from about 10% (by total weight of the formulation) to about 89% (by total weight of the formulation), more desirably from about 30% (by total weight of the formulation) to about 80% (by total weight of the formulation), and still more desirably from about 60% (by total weight of the formulation) to about 80% (by total weight of the formulation).

Suitable emollients for use in the lubricating formulations of the present invention are typically substantially water free. Although the emollient may contain trace amounts of water as a contaminant without substantially harming the lubricating formulation, it is preferred that the amount of water be less than about 5% by weight of the emollient component of the lubricating formulation to reduce the likelihood of microbial growth and product destruction.

Suitable emollients for use in the lubricating formulations of the present invention include, for example, petrolatum, mineral oil, mineral jelly, isoparaffins, vegetable oils such as avocado oil, borage oil, canola oil, castor oil, chamomile, coconut oil, corn oil, cottonseed oil, evening primrose oil, safflower oil, sunflower oil, soybean oil, sweet almond, and the like, lanolin, partially hydrogenated vegetable oils, polydimethylsiloxanes such as methicone, cyclomethicone, dimethicone, dimethiconol, and trimethicone, organo-siloxanes (i.e., where the organic functionality can be selected from alkyl, phenyl, amine, polyethylene glycol, amine-glycon, alkylaryl, carboxal, and the like), silicone elastomer, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, Guerbet alcohols, Guerbet Acids, Guerbet Esters, and other cosmetically acceptable emollients.

Additionally, some emollients are solids at room temperature, and may have a dual benefit of being solid emollients (at room temperature) as well as structuring agents. Compounds that act as both emollients and structuring agents include, for example, $C_{14}$-$C_{28}$ fatty acid esters (esters of $C_{12}$-$C_{28}$ fatty acids and $C_{12}$-$C_{28}$ fatty alcohols), $C_{14}$-$C_{28}$ fatty alcohols, $C_{14}$-$C_{28}$ fatty acids, $C_{14}$-$C_{28}$ fatty acid ethoxylates, $C_{14}$-$C_{28}$ fatty ethers and $C_{16}$-$C_{30}$ alkyl siloxanes.

The structurant utilized in the lubricating formulations described herein help to immobilize the emollient and other components on the surface of the tissue paper where they are of greatest value. Because some emollients are fluids at room temperature, they may tend to flow or migrate away from the surface of the tissue paper into the interior of the tissue paper where they are of limited value and may tend to decrease the strength of the tissue due to debonding. The structurant reduces the ability of the emollient (and other components) from migrating and keeps the emollient primarily on the surface of the tissue paper. The structurant is present in the lubricating formulations in an amount of from about 10% (by total weight of the formulation) to about 50% (by total weight of the formulation), desirably from about 20% (by total weight of the formulation) to about 40% (by total weight of the formulation).

Suitable structurants for use in the lubricating formulations disclosed herein have a melting point of about 45° C. to about 85° C. and may include, for example, waxes including animal waxes, vegetable waxes, mineral waxes, synthetic waxes, and polymers. Exemplary structurants include bayberry wax, beeswax, stearyl dimethicone, stearyl trimethicone, $C_{20}$-$C_{22}$ dimethicone, $C_{20}$-$C_{22}$ trimethicone, $C_{24}$-$C_{28}$ dimethicone, $C_{20}$-$C_{22}$ trimethicone, $C_{30}$ alkyl dimethicone, candelilla wax, carnauba, ceresin, cetyl esters, stearyl benzoate, behenyl benzoate, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, cerasin, ozokerite paraffin, PEG-6 beeswax, PEG-8 beeswax, rezowax, rice bran wax, shellac wax, spent grain wax, spermaceti wax, synthetic spermaceti wax, synthetic beeswax, synthetic candelilla wax, synthetic carnuba wax, synthetic japan wax, synthetic jojoba wax, $C_{14}$-$C_{28}$ fatty acid ethoxylates and $C_{14}$-$C_{28}$ fatty ethers, $C_{14}$-$C_{28}$ fatty alcohols, $C_{14}$-$C_{28}$ fatty acids, polyethylene, oxidized polyethylene, ethylene-alpha olefin copolymers, ethylene homopolymers such as Petrolite EP copolymers from Baker Hughes Inc., (Sugar Land Tex.), $C_{18}$-$C_{45}$ olefins, poly alpha olefins such as Vybar Polymers from Baker Hughes Inc. or Okerin Polymers from Honeywell Specialty Chemicals, (Duluth, Ga.), hydrogenated vegetable oils, polyhydroxy fatty acid esters, polyhydroxy fatty acid amides, ethoxylated fatty alcohols and esters of $C_{12}$-$C_{28}$ fatty acids, and $C_{12}$-$C_{28}$ fatty alcohols.

The rheology enhancers utilized in the lubricating formulation increase the melt point viscosity of the lubricating formulation so that the formulation readily remains on the surface of the tissue and does not substantially migrate into the interior of the tissue matrix, while substantially not affecting the transfer of the lubricating formulation to the skin. Additionally, the rheology enhancers help the lubricating formulation to maintain a high viscosity at elevated temperatures, such as those encountered during storage and transportation. Desirably, the rheology enhancer increases the viscosity of the lubricating formulation by at least about 50%, more desirably at least about 500%, and even more desirably at least about 1000%. The rheology enhancer is present in the lubricating formulation in an amount of from about 0.1% (by total weight of the formulation) to about 40% (by total weight of the formulation), desirably from about 0.5% (by total weight of the formulation) to about 30% (by total weight of the formulation) and even more desirably from about 1% (by total weight of the formulation) to about 25% (by total weight of the formulation).

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers.

The lubricating formulations described herein have specific melt point and process temperature viscosities, as defined herein. These viscosities are important for at least two reasons. First, the higher the melt point or process temperature viscosity, the less likely the lubricating formulation is to penetrate into the inner surface of the tissue matrix. The less lubricating formulation that is able to penetrate into the tissue matrix, results in more lubricating formulation on the surface of the tissue that can transfer to the user's skin. Secondly, the higher the viscosity of the formulation at or above the melting point of the formulation, the less likely the formulation will be to migrate at typical or adverse storage or temperature conditions.

The lubricating formulations described herein have a melt point viscosity of from about 5000 cPs to about 1,000,000 cPs, desirably from about 50,000 cPs to about 800,000 cPs, and more desirably from about 100,000 cPs to about 500,000 cPs. As used herein, the term "melt point viscosity" means the viscosity of the formulation at the point in time when the formulation visually becomes a liquid. Lubricating formulations having melt point viscosities in these ranges significantly improve the ability of the lubricating formulation to remain on the surface of the tissue and the formulation maintains a high viscosity at elevated temperatures, such as those encountered during storage and shipment.

Additionally, to improve application to the surface of the tissue, the lubricating formulations described herein have a process temperature viscosity of from about 50 cPs to about 50,000 cPs, desirably from about 75 cPs to about 10,000 cPs, and more desirably from about 80 cPs to about 5,000 cPs. The process temperature is typically from about 5° C. to about 20° C. above the melting point of the lubricating formulation.

The lubricating formulations described herein may be applied to one surface of a facial or bath tissue, or may be applied to both surfaces of a facial or bath tissue. Any of a number of known methods that substantially evenly distribute the lubricating formulation may be used to treat the tissue product. Such methods include, for example, spraying, printing, coating, extrusion, ink jet printing, and combinations thereof. Regardless of how the lubricating formulation is applied to the tissue product, it should be applied in such a manner that the tissue does not become oversaturated with the lubricating formulation. If oversaturation occurs, there is a greater potential for debonding of the tissue paper to occur, which leads to a substantial decrease in the tensile strength of the paper and poor aesthetic performance.

Regardless of whether the lubricating formulation is introduced onto one or both surfaces of the tissue product, the lubricating formulation is typically introduced onto the tissue product in an amount of from about 1% by dry weight of the tissue product to about 30% by dry weight of the tissue product, desirably from about 1% by dry weight of the tissue product to about 20% by dry weight of the tissue product, and more desirably from about 1% by dry weight of the tissue product to about 10% by dry weight of the tissue product.

The lubricating formulation can be applied to the surface of the tissue product in various methods known in the art. For example, the lubricating formulation can be applied in a continuous pattern, discontinuous pattern, uniformly spaced deposits, and/or in a designed pattern comprising stripes, dots, logos, figures, and the like.

The lubricating formulations described herein have a penetration hardness such that the lubricating formulation is stable on the surface of the tissue product, yet easily transferred to the skin of the user during use. For purposes herein, penetration hardness is the needle penetration in millimeters according to ASTM D 1321, Needle Penetration of Petroleum Waxes. Lower needle penetration hardness values correspond to harder materials. The penetration hardness of the formulations of this invention can be from about 5 to 360 millimeters, more specifically from about 5 to about 200 millimeters, more specifically from about 20 to about 150 millimeters, and still more specifically from about 40 to about 140 millimeters, and more specifically from about 60 to about 120 millimeters. (Formulations having a needle penetration hardness greater than 360 millimeters cannot be measured using ASTM method D 1321). The hardness of the lubricating formulations described herein is important for at least two reasons. First, the softer the formulation, the more mobile the formulation will be, making the formulation more likely to migrate to the interior of the tissue, which, as discussed above, is not desirable. Second, softer formulations tend to be more greasy/oily to the touch, which is also less desirable. In general, formulations having a needle penetration hardness of from about 200 to 360 millimeters feel creamy to slightly greasy with less smoothness (depending on additives). Formulations that have needle penetration hardness values of from about 5 to about 200 millimeters feel silky to creamy and very smooth (depending on additives).

Along with the components described above, an optional hydrophilic surfactant may be added to the lubricating formulations described herein to enhance the wettability of the treated tissue paper. Depending upon the composition of the lubricating formulation, and specifically which structurant is utilized, it may be advantageous to add a hydrophilic surfactant to ensure that the tissue paper has sufficient wettability upon use. This may be particularly important when the tissue paper is bath tissue.

Suitable hydrophilic surfactants should be miscible with the emollient, structurant, and rheology enhancer so as to form a substantially homogeneous mixture. Desirably, the hydrophilic surfactant should be mild and substantially non-irritating to skin such that individuals with sensitive skin can easily use the product comprising the lubricating formulation. Generally, the hydrophilic surfactant will be a nonionic surfactant to be not only non-irritating to the skin, but also to avoid other undesirable affects on the tissue paper, such as a reduction in tensile strength.

Suitable nonionic surfactants should be substantially non-migratory after the lubricating composition is applied to the tissue paper. Typically, the nonionic surfactant will have a hydrophilic/lipophilic balance value in the range from about 4 to about 20, preferably from about 2 to about 7. It is also advantageous for the nonionic surfactant to have a melting point greater than about 30° C. to ensure stability in the product.

Nonionic surfactants suitable for incorporation into the lubricating formulations described herein include alkylglycosides, alkylglycoside ethers, alkylpolyethoxylated esters, ethoxylated sorbitan mono-, di-, and/or tri-esters of $C_{12}$-$C_{18}$ fatty acids having an average degree of ethoxylation of from about 2 to about 20, and silicone copolymers. The lubricating formulation may comprise from about 1% (by total weight of the formulation) to about 50% (by total weight of the formulation), desirably from about 1% (by total weight of the formulation) to about 20% (by total weight of the formulation) of the hydrophilic surfactant.

In order to better enhance the benefits to consumers, additional ingredients can be incorporated into the lubrication formulation described herein. The classes of ingredients and their corresponding benefits include, without limitation: antifoaming agents (reduce the tendency of foaming during processing); antimicrobial actives; antivirul actives; antifungal actives; antiseptic actives; antioxidants (product integrity to prevent oxidation of natural oils and other ingredients on the formulation or composition); astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product including vitamins); colorants (impart color to the product); deodorants (reduce or eliminate unpleasant odor and protect against the formation of malodor on body surfaces); film formers (to hold active ingredients on the skin by producing a continuous film on skin upon drying); fragrances (consumer appeal); lubricants, such as silicones and organomodified silicones; natural moisturizing agents (NMF) and other skin moisturizing ingredients known in the art; skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (liquids employed to dissolve components found useful in the cosmetics or drugs); and UV absorbers.

EXAMPLE 1

In this Example, several lubricating formulations were prepared and evaluated for penetration hardness, viscosity at 55° C. (1/sec) and viscosity at 60° C. (1/sec). The composition of each of the lubricating formulations tested are set forth in the tables below, along with the hardness and viscosity results.

TABLE 1

| Component | A Wt. % | B Wt. % | C Wt. % | D Wt. % |
|---|---|---|---|---|
| Petrolatum | 76.00 | 78.00 | 76.00 | 83.00 |
| Alpha Olefin Polymer ($C_{24}$-$C_{28}$) | 12.00 | 7.00 | 3.00 | 3.00 |
| Ethylene/Vinyl Acetate Copolymer with Polyethylene | 12.00 | 15.00 | 18.00 | 12.00 |
| Hardness | 75 | 110 | 88 | 71 |
| Viscosity @ 55° C. 0.5 1/sec | 17,100 | 23,000 | 63,500 | 10,200 |
| Viscosity @ 60° C., 0.5 1/sec | 171 | 206 | 2990 | 1670 |

TABLE 2

| Component | A Wt. % | B Wt. % | C Wt. % | D Wt. % | E Wt. % | F Wt. % |
|---|---|---|---|---|---|---|
| Petrolatum | 80.00 | 80.00 | 78.00 | 77.00 | 80.00 | 79.00 |
| Polyethylene and Ethylene/Vinyl Acetate Copolymer | 13.00 | 15.00 | 15.00 | 18.00 | 15.00 | 15.00 |
| Alpha Olefin Polymer ($C_{24}$-$C_{28}$) | 7.00 | 5.00 | 7.00 | 5.00 | 3.00 | 3.00 |
| Ethylene/Vinyl Acetate Copolymer (ELVAX 410 Resin) | 0.00 | 0.00 | 0.00 | 0.00 | 2.00 | 3.00 |
| Hardness | 76 | 91 | 80 | 83 | 95 | 83 |
| Viscosity @ 55° C., 0.5 1/sec | 5310 | 13,200 | 20,630 | 171,700 | 12,010 | 236,200 |
| Viscosity @ 60° C., 0.5 1/sec | 1180 | 595 | 814 | 1153 | 2663 | 1427 |

TABLE 3

| Component | A Wt. % | B Wt. % | C Wt. % | D Wt. % |
|---|---|---|---|---|
| Petrolatum | 81.00 | 75.00 | 80.00 | 80.00 |
| Ethylene/Vinyl Acetate Copolymer (ELVAX 410 Resin) | 0.00 | 0.00 | 2.00 | 2.00 |
| Polyethylene and Ethylene/Vinyl Acetate Copolymer | 12.00 | 10.00 | 15.00 | 15.00 |
| Hydrogenated Cottonseed Oil | 0.00 | 15.00 | 3.00 | 0.00 |
| Hardness | 88 | 102 | 86 | 86 |
| Viscosity @ 55° C., 0.5 1/sec | 3184 | 1591 | 18,430 | 8591 |
| Viscosity @ 60° C., 0.5 1/sec | 169 | 44 | 1846 | 1105 |

TABLE 4

| Component | A Wt. % | B Wt. % | C Wt. % | D Wt. % | E Wt. % | F Wt. % |
|---|---|---|---|---|---|---|
| Mineral Oil | 54.8 | 49.8 | 44.8 | 33.5 | 44.9 | 44.9 |
| Mineral Oil and Styrene (Versagel M-750) | 5 | 10 | 15 | 30 | 14.9 | 14.9 |
| Stearyl Alcohol | 18 | 18 | 18 | 18 | 9 | 27 |
| Microcrystalline Wax | 0 | 0 | 0 | 0 | 13.5 | 4.5 |
| Isopropyl Palmitate | 3 | 3 | 3 | 3 | 0 | 0 |
| Dimethicone 200 (Dow) | 1 | 1 | 1 | 1 | 0 | 0 |
| Alkyl Silicone Wax (Stearyl Dimethicone) | 0 | 0 | 0 | 0 | 4 | 4 |
| Aloe Vera | 0.1 | 0.1 | 0.1 | 0 | 0.1 | 0.1 |
| Vitamin E Acetate | 0.1 | 0.1 | 0.1 | 0 | 0.1 | 0.1 |
| Viscosity @ 55° C., 0.5 1/sec | 23 | 33 | 20.5 | Not Done | 126 | 92 |
| Viscosity @ 60° C., 0.5 1/sec | 17.5 | 27 | 17 | Not Done | 77 | 58 |

TABLE 5

| Component | A Wt. % | B Wt. % |
|---|---|---|
| Petrolatum | 80 | 77 |
| Ethylene/Vinyl Acetate Copolymer with Polyethylene | 10 | 10 |
| Alpha Olefin Polymer ($C_{24}$-$C_{28}$) | 7 | 7 |
| Fumed Silica | 3 | 3 |
| Polyisobutene | 0 | 3 |
| Hardness | 134 | 140 |
| Viscosity @ 55° C., 0.5 1/sec | 10,175 | 12,025 |
| Viscosity @ 60° C., 0.5 1/sec | 10,945 | 12,950 |

TABLE 6

| Component | A Wt. % | B Wt. % | C Wt. % |
|---|---|---|---|
| Petrolatum | 75 | 0 | 0 |
| Versagel PT200 (Petrolatum and styrene copolymer) | 0 | 80 | 75 |
| Ethylene/Vinyl Acetate Copolymer and Polyethylene | 10 | 0 | 10 |
| Stearyl Behenate | 15 | 20 | 15 |
| Hardness | N/A | 76 | 92 |
| Viscosity @ 55° C. | <50 | 7622 | 3130 |
| Viscosity @ 60° C. | <50 | 7078 | 2593 |

In view of the above, it will be seen that the several objects of the invention are achieved. As various changes could be made in the above-described tissue products without departing from the scope of the invention, it is intended that all matter contained in the above description be interpreted as illustrative and not in a limiting sense.

What is claimed is:

1. A tissue product comprising a fibrous substrate material and a lubricating formulation, the lubricating formulation being present on the tissue product in an amount of from about 1% (by weight of the dry tissue) to about 30% (by weight of the dry tissue) and comprising from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the forulation) of a rheology enhancer, wherein the rheology enhancer is selected from the group consisting of ethylene/propylene/styrene copolymers alone or in combination with mineral oil or petrolatum; butylene/ethylene/styrene copolymers alone or in combination with mineral oil or petrolatum; mineral oil and styrene; and combinations thereof.

2. The tissue product as set forth in claim 1 wherein the lubricating formulation is present on the tissue product in an amount of from about 1% (by weight of the dry tissue) to about 20% (by weight of the dry tissue).

3. The tissue product as set forth in claim 1 wherein the lubricating formulation is present on the tissue product in an amount of from about 1% (by weight of the dry tissue) to about 10% (by weight of the dry tissue).

4. The tissue product as set forth in claim 1 wherein the emollient is present in an amount of from about 30% (by total weight of the formulation) to about 80% (by total weight of the formulation).

5. The tissue product as set forth in claim 1 wherein the emollient is present in an amount of from about 60% (by total weight of the formulation) to about 80% (by total weight of the formulation).

6. The tissue product as set forth in claim 1 wherein the structurant is present in an amount of from about 20% (by total weight of the formulation) to about 40% (by total weight of the formulation).

7. The tissue product as set forth in claim 1 wherein the rheology enhancer is present in an amount of from about 0.5% (by total weight of the formulation) to about 30% (by total weight of the formulation).

8. The tissue product as set forth in claim 1 wherein the rheology enhancer is present in an amount of from about 1% (by total weight of the formulation) to about 25% (by total weight of the formulation).

9. The tissue product as set forth in claim 1 wherein the lubricating formulation has a melt point viscosity of from about 5000 cPs to about 1,000,000 cPs.

10. The tissue product as set forth in claim 1 wherein the lubricating formulation has a melt point viscosity of from about 50,000 cPs to about 800,000 cPs.

11. The tissue product as set forth in claim 1 wherein the lubricating formulation has a melt point viscosity of from about 100,000 cPs to about 500,000 cPs.

12. The tissue product as set forth in claim 1 wherein the lubricating formulation has a process temperature viscosity of from about 50 cPs to about 50,000 cPs.

13. The tissue product as set forth in claim 1 wherein the lubricating formulation has a process temperature viscosity of from about 75 cPs to about 10,000 cPs.

14. The tissue product as set forth in claim 1 wherein the lubricating formulation has a process temperature viscosity of from about 80 cPs to about 5,000 cPs.

15. The tissue product as set forth in claim 1 wherein the lubricating formulation has a penetration hardness of from about 40 to about 140.

16. The tissue product as set forth in claim 1 wherein the lubricating formulation has a penetration hardness of from about 60 to about 120.

17. The tissue product as set forth in claim 1 further comprising a hydrophilic surfactant.

18. The tissue product as set forth in claim 1 wherein the lubricating formulation further comprises an additional ingredient selected from the group consisting of antifoaming agents, antimicrobial actives, antivirul actives, antifungal actives, antiseptic actives, antioxidants, humectants, cosmetic astringents, drug astringents, biological additives, colorants, deodorants, film formers, fragrances, lubricants, natural moisturizing agents, skin conditioning agents, skin exfoliating agents, skin protectants, solvents, hydrophilic surfactants, and UV absorbers.

19. The tissue product as set forth in claim 1 wherein emollient is selected from the group consisting of petrolatum, mineral oil, mineral jelly, isoparaffins, vegetable oils, avocado oil, borage oil, canola oil, castor oil, chamomile, coconut oil, corn oil, cottonseed oil, evening primrose oil, safflower oil, sunflower oil, soybean oil, sweet almond, and the like, lanolin, partially hydrogenated vegetable oils, polydimethylsiloxanes, methicone, cyclomethicone, dimethicone, dimethiconol, trimethicone, organo-siloxanes, silicone elastomer, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, Guerbet alcohols, Guerbet Acids, Guerbet Esters, and combinations thereof.

20. The tissue product as set forth in claim 1 wherein the structurant has a melting point of from about 45° C. to about 85° C.

21. The tissue product as set forth in claim 1 wherein the structurant is selected from the group consisting of animal waxes, vegetable waxes, mineral waxes, synthetic waxes, polymers, bayberry wax, beeswax, stearyl dimethicone, stearyl trimethicone, $C_{20}$-$C_{22}$ dimethicone, $C_{20}$-$C_{22}$ trimethicone, $C_{24}$-$C_{28}$ dimethicone, $C_{20}$-$C_{22}$ trimethicone, $C_{30}$ alkyl dimethicone, candelilla wax, carnauba, ceresin, cetyl esters, stearyl benzoate, behenyl benzoate, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, synthetic spermaceti wax, synthetic beeswax, synthetic candelilla wax, synthetic carnuba wax, synthetic japan wax, synthetic jojoba wax, $C_{14}$-$C_{28}$ fatty acid ethoxylates and $C_{14}$-$C_{28}$ fatty ethers, $C_{14}$-$C_{28}$ fatty alcohols, $C_{14}$-$C_{28}$ fatty acids, polyethylene, oxidized polyethylene, ethylene-alpha olefin copolymers, ethylene homopolymers, $C_{18}$-$C_{45}$ olefins, poly alpha olefins, hydrogenated vegetable oils, polyhydroxy fatty acid esters, polyhydroxy fatty acid amides, ethoxylated fatty alcohols and esters of $C_{12}$-$C_{28}$ fatty acids, and $C_{12}$-$C_{28}$ fatty alcohols, and combinations thereof.

22. The tissue product as set forth in claim 1 wherein the lubricating formulation is introduced onto the tissue by a method selected from the group consisting of spraying, slot coating, gravure coating, flexigraphic coating, ink jet printing, melt blown coating, and combinations thereof.

23. The tissue product as set forth in claim 1 wherein the tissue product is a facial tissue.

24. The tissue product as set forth in claim 1 wherein the tissue product is a bath tissue.

25. The tissue product as set forth in claim 1 wherein the tissue product is a paper towel.

26. The tissue product as set forth in claim 1 wherein the tissue product is a napkin.

27. The tissue product as set forth in claim 1 wherein the tissue product is a single-ply tissue product.

28. The tissue product as set forth in claim 1 wherein the tissue product is a multi-ply tissue product.

29. A tissue product comprising a fibrous substrate material and a lubricating formulation, the lubricating formulation being present on the tissue product in an amount of from about 1% (by weight of the dry tissue) to about 30% (by weight of the dry tissue) and comprising from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the formulation) of a rheology enhancer, wherein the lubricating formulation has a melt point viscosity of from about 5000 cPs to about 1,000,000 cPs and a process temperature viscosity of from about 50 cPs to about 50,000 cPs, wherein the rheology enhancer is selected from the group consisting of ethylene/propylene/styrene copolymers alone or in combination with mineral oil or petrolatum; butylene/ethylene/styrene copolymers alone or in combination with mineral oil or petrolatum; mineral oil and styrene; and combinations thereof.

30. The tissue product as set forth in claim 29 wherein the lubricating formulation is present on the tissue product in an amount of from about 1% (by weight of the dry tissue) to about 20% (by weight of the dry tissue).

31. The tissue product as set forth in claim 29 wherein the lubricating formulation is present on the tissue product in an amount of from about 1% (by weight of the dry tissue) to about 10% (by weight of the dry tissue).

32. The tissue product as set forth in claim 29 wherein the emollient is present in an amount of from about 30% (by total weight of the formulation) to about 80% (by total weight of the formulation).

33. The tissue product as set forth in claim 29 wherein the emollient is present in an amount of from about 60% (by total weight of the formulation) to about 80% (by total weight of the formulation).

34. The tissue product as set forth in claim 29 wherein the structurant is present in an amount of from about 20% (by total weight of the formulation) to about 40% (by total weight of the formulation).

35. The tissue product as set forth in claim 29 wherein the rheology enhancer is present in an amount of from about 0.5% (by total weight of the formulation) to about 30% (by total weight of the formulation).

36. The tissue product as set forth in claim 29 wherein the rheology enhancer is present in an amount of from about 1% (by total weight of the formulation) to about 25% (by total weight of the formulation).

37. The tissue product as set forth in claim 29 wherein the melt point viscosity is from about 50,000 cPs to about 800,000 cPs.

38. The tissue product as set forth in claim 29 wherein the melt point viscosity is from about 100,000 cPs to about 500,000 cPs.

39. The tissue product as set forth in claim 29 wherein the process temperature viscosity is from about 75 cPs to about 10,000 cPs.

40. The tissue product as set forth in claim 29 wherein the process temperature viscosity is from about 80 cPs to about 5,000 cPs.

41. The tissue product as set forth in claim 29 wherein the lubricating formulation has a penetration hardness of from about 40 to about 140.

42. The tissue product as set forth in claim 29 wherein the lubricating formulation has a penetration hardness of from about 60 to about 120.

43. The tissue product as set forth in claim 29 further comprising a hydrophilic surfactant.

44. The tissue product as set forth in claim 29 wherein emollient is selected from the group consisting of petrolatum, mineral oil, mineral jelly, isoparaffins, vegetable oils, avocado oil, borage oil, canola oil, castor oil, chamomile, coconut oil, corn oil, cottonseed oil, evening primrose oil, safflower oil, sunflower oil, soybean oil, sweet almond, and the like, lanolin, partially hydrogenated vegetable oils, polydimethylsiloxanes, methicone, cyclomethicone, dimethicone, dimethiconol, trimethicone, organo-siloxanes, silicone elastomer, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, Guerbet alcohols, Guerbet Acids, Guerbet Esters, and combinations thereof.

45. The tissue product as set forth in claim 29 wherein the structurant has a melting point of from about 45° C. to about 85° C.

46. The tissue product as set forth in claim 29 wherein the structurant is selected from the group consisting of animal waxes, vegetable waxes, mineral waxes, synthetic waxes, polymers, bayberry wax, beeswax, stearyl dimethicone, stearyl trimethicone, $C_{20}$-$C_{22}$ dimethicone, $C_{20}$-$C_{22}$ trimethicone, $C_{24}$-$C_{28}$ dimethicone, $C_{20}$-$C_{22}$ trimethicone, $C_{30}$ alkyl dimethicone, candelilla wax, carnauba, ceresin, cetyl esters, stearyl benzoate, behenyl benzoate, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acide wax, motan wax, ouricury wax, ozokerite parrafin, PEG-6 beeswax, PEG-8 beeswax, rezowax, rice bran wax, shellac wax, spent grain wax, spermaceti wax, synthetic spermaceti wax, synthetic beeswax, synthetic candelilla wax, synthetic carnuba wax, synthetic japan wax, synthetic jojoba wax, $C_{14}$-$C_{28}$ fatty acid ethoxylates and $C_{14}$-$C_{28}$ fatty ethers, $C_{14}$-$C_{28}$ fatty alcohols, $C_{14}$-$C_{28}$ fatty acids, polyethylene, oxidized polyethylene, ethylene-alpha olefin copolymers, ethylene homopolymers, $C_{18}$-$C_{45}$ olefins, poly alpha olefins, hydrogenated vegetable oils, polyhydroxy fatty acid esters, polyhydroxy fatty acid amides, ethoxylated fatty alcohols and esters of $C_{12}$-$C_{28}$ fatty acids, and $C_{12}$-$C_{28}$ fatty alcohols, and combinations thereof.

47. The tissue product as set forth in claim 29 wherein the lubricating formulation further comprises an additional ingredient selected from the group consisting of antifoaming agents, antivirul actives, antimicrobial actives, antifungal actives, antiseptic actives, antioxidants, cosmetic astringents, drug astringents, biological additives, colorants, deodorants, film formers, fragrances, lubricants, natural moisturizing agents, skin conditioning agents, skin exfoliating agents, skin protectants, solvents, hydrophilic surfactants, and UV absorbers.

48. The tissue product as set forth in claim 29 wherein the lubricating formulation is introduced onto the tissue by a method selected from the group consisting of spraying, slot coating, gravure coating, ink jet printing, flexi graphic coating, melt blown coating, and combinations thereof.

49. The tissue product as set forth in claim 29 wherein the tissue product is a facial tissue.

50. The tissue product as set forth in claim 29 wherein the tissue product is a bath tissue.

51. The tissue product as set forth in claim 29 wherein the tissue product is a paper towel.

52. The tissue product as set forth in claim 29 wherein the tissue product is a napkin.

53. The tissue product as set forth in claim 29 wherein the tissue product is a single-ply tissue product.

54. The tissue product as set forth in claim 29 wherein the tissue product is a multi-ply tissue product.

55. A method of manufacturing a facial tissue comprising introducing a lubricating formulation onto a tissue substrate, the lubricating formulation being present on the tissue substrate in an amount of from about 1% (by weight of the dry tissue) to about 30% (by weight of the dry tissue) and comprising from about 10% (by total weight of the formulation) to about 89% (by total weight of the formulation) of an emollient, from about 10% (by total weight of the formulation) to about 50% (by total weight of the formulation) of a structurant, and from about 0.1% (by total weight of the formulation) to about 40% (by total weight of the formulation) of a rheology enhancer, wherein the lubricating formulation has a melt point viscosity of from about 5000 cPs to about 1,000,000 cPs and a process temperature viscosity of from about 50 cPs to about 50,000 cPs, wherein the rheology enhancer is selected from the group consisting of ethylene/propylene/styrene copolymers alone or in combination with mineral oil or petrolatum; butylene/ethylene/styrene copolymers alone or in combination with mineral oil or petrolatum; mineral oil and styrene; and combinations thereof.

56. The method as set forth in claim 55 wherein the emollient is present in an amount of from about 30% (by total weight of the formulation) to about 80% (by total weight of the formulation).

57. The method as set forth in claim 55 wherein the emollient is present in an amount of from about 60% (by total weight of the formulation) to about 80% (by total weight of the formulation).

58. The method as set forth in claim 55 wherein the structurant is present in an amount of from about 20% (by total weight of the formulation) to about 40% (by total weight of the formulation).

59. The method as set forth in claim 55 wherein the rheology enhancer is present in an amount of from about 0.5% (by total weight of the formulation) to about 30% (by total weight of the formulation).

60. The method as set forth in claim 55 wherein the rheology enhancer is present in an amount of from about 1% (by total weight of the formulation) to about 25% (by total weight of the formulation).

61. The method as set forth in claim 55 wherein the lubricating formulation is introduced onto the tissue substrate by a method selected from the group consisting of spraying, ink jet printing, slot coating, gravure coating, flexi-graphic coating, melt blown coating, and combinations thereof.

62. The tissue product as set forth in claim 1 wherein the rheology enhancer is selected from the group consisting of mineral oil and ethylene/propylene/styrene copolymers; mineral oil and butylene/ethylene/styrene copolymers; mineral oil and styrene; and combinations thereof.

63. The tissue product as set forth in claim 29 wherein the rheology enhancer is selected from the group consisting of mineral oil and ethylene/propylene/styrene copolymers; mineral oil and butylene/ethylene/styrene copolymers; mineral oil and styrene; and combinations thereof.

64. The method as set forth in claim 55 wherein the rheology enhancer is selected from the group consisting of mineral oil and ethylene/propylene/styrene copolymers; mineral oil and butylene/ethylene/styrene copolymers; mineral oil and styrene; and combinations thereof.

* * * * *

UNITED STATES PATENT AND TRADEMARK OFFICE
CERTIFICATE OF CORRECTION

PATENT NO. : 7,485,373 B2
APPLICATION NO. : 10/659968
DATED : February 3, 2009
INVENTOR(S) : Krzysik et al.

It is certified that error appears in the above-identified patent and that said Letters Patent is hereby corrected as shown below:

On Title Page in the Abstract, delete "1,000,000 cps" and insert therefor -- 1,000,000 cPs --.

In the Specification, column 2, line 56, delete "1,000,000 cps" and insert therefor -- 1,000,000 cPs --.

In Claim 1, column 14, line 26, delete "forulation) of a rheology" insert therefor -- formulation) of a rheology --.

Signed and Sealed this

Nineteenth Day of May, 2009

JOHN DOLL
*Acting Director of the United States Patent and Trademark Office*